US00PP28061P3

(12) United States Plant Patent
Vanderhaegen

(10) Patent No.: US PP28,061 P3
(45) Date of Patent: May 30, 2017

(54) ***RHODODENDRON* PLANT NAMED 'HORT13'**

(50) Latin Name: *Rhododendron simsii*
Varietal Denomination: HORT13

(71) Applicant: Johan Vanderhaegen, Kruishoutem (BE)

(72) Inventor: Johan Vanderhaegen, Kruishoutem (BE)

(73) Assignee: Hortibreed NV, Lochristi (BE)

( * ) Notice: Subject to any disclaimer, the term of this patent is extended or adjusted under 35 U.S.C. 154(b) by 0 days.

(21) Appl. No.: 14/999,052

(22) Filed: Mar. 23, 2016

(65) Prior Publication Data

US 2016/0309636 P1 Oct. 20, 2016

(30) Foreign Application Priority Data

Apr. 14, 2015 (QZ) ..... PBR 2015/0839

(51) Int. Cl.
*A01H 5/00* (2006.01)

(52) U.S. Cl.
USPC ..... Plt./239

(58) Field of Classification Search
USPC ..... Plt./239
See application file for complete search history.

*Primary Examiner* — Annette Para

(57) ABSTRACT

A new cultivar of *Rhododendron* plant named 'HORT13' that is characterized by green flower buds that open slowly, light pink double flowers, late flowering and a long flowering period.

1 Drawing Sheet

Botanical classification: *Rhododendron simsii.*
Variety denomination: 'HORT13'.

BACKGROUND OF THE INVENTION

The present invention relates to a new and distinct cultivar of *Rhododendron* plant botanically known as *Rhododendron simsii* and hereinafter referred to by the cultivar name 'HORT13'.

The new cultivar is the product of a breeding program conducted by the inventor in a cultivated area of Kruishoutem, Belgium. The objective of the breeding program is to develop new *Rhododendron* cultivars that have long lasting flowers and slowly opening flower buds.

'HORT13' originated from the crossing of the female or seed parent *Rhododendron simsii* 'Christine Matton' (U.S. Plant Pat. No. 11,693) and the male or pollen parent a proprietary selection of *Rhododendron simsii* identified as '99367' (not patented). The crossing was conducted in 2002. The cultivar 'HORT13' was selected by the inventor in 2004 as a single plant within the progeny of the stated cross in a greenhouse environment in a cultivated area of Kruishoutem, Belgium.

Asexual reproduction of the new cultivar 'HORT13' by cuttings was first performed in 2004 in Kruishoutem, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Rhododendron* cultivar 'HORT13'. These traits in combination distinguish 'HORT13' as a new and distinct cultivar.

1. *Rhododendron* 'HORT13' exhibits green flower buds that open slowly.
2. *Rhododendron* 'HORT13' exhibits light pink double flowers.
3. *Rhododendron* 'HORT13' exhibits late flowering.
4. *Rhododendron* 'HORT13' exhibits a long flowering period.

The closest comparison varieties are *Rhododendron* 'HORT10' (not patented) and *Rhododendron* 'HORT14' (U.S. Plant patent application Ser. No. 14/999,054).

'HORT13' is different than 'HORT10' in having light pink flowers. In contrast, the flowers of 'HORT10' are white.

'HORT13' is different than 'HORT14' in having lighter pink flowers. In contrast, the flowers of 'HORT14' have pink petals with yellow-green tips.

In comparison to the female parent plant 'Christine Matton', 'HORT13' is different in having lighter pink flowers, weaker lateral branches and duller leaves. In contrast, the flowers of 'Christine Matton' are salmon pink in color.

In comparison to the male parent plant '99367', 'HORT13' is different in having light pink flowers. In contrast, the flowers of '99367' are red in color and have hose in hose sepals.

BRIEF DESCRIPTION OF THE DRAWING

The accompanying photograph illustrates the distinguishing traits of *Rhododendron* 'HORT13'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Rhododendron* cultivar named 'HORT13'. Data was collected in Kruishoutem, Belgium from 24 month old greenhouse grown plants in 1.0 liter containers. The time of year was Spring and the average temperature was 22° Centigrade during the day and 18° Centigrade at night. The light level was 5000 Klux and there were no photoperiodic treatments. Color determinations are in accordance with The Royal Horticultural Society Colour Chart 2001 edition, except where general color terms of ordinary dictionary significance are used. The growing requirements are similar to the species. 'HORT13' has not been tested under all possible conditions and phenotypic differences may be observed with variations in environmental, climatic, and cultural conditions, however, without any variance in genotype.

Botanical classification: *Rhododendron simsii* 'HORT13'.

Use: Ornamental perennial shrub.

Parentage: 'HORT13' is a cross of the female or seed parent *Rhododendron* 'Christine Matton' and the male or pollen parent *Rhododendron* '99367'.

Vigor: Moderately strong.

Growth rate: Approximately 8 cm. in height and 15 cm. in width per year.

Growth habit: Flat, outwardly spreading growth habit.

Plant shape: Flattened globose.

Suitable container size: 1.0 liter container.

Height: Average 20 cm. in height.

Width: Average 40 cm. in width.

Hardiness: USDA Zone 9.

Propagation: Terminal cuttings.

Time to initiate roots: Approximately 30 days to produce roots on an initial cutting.

Time to produce a rooted cutting or liner: Approximately 60 days.

Root system: Fine and fibrous.

Stem:

*Branching habit.*—Freely branching.
*Average number of lateral branches.*—3.
*Pinching.*—Yes.
*Lateral branch diameter.*—1.5 mm. in diameter.
*Lateral branch length.*—9 cm. in length.
*Lateral branch strength.*—Moderate to weak.
*Stem color.*—145A, older stems 200D.
*Pubescence.*—Sparse, length 1.5 mm., color 175B to 175C.
*Internode length.*—11 mm. between nodes.
*Shape.*—Round.
*Surface.*—Dull.
*Stem strength.*—Moderate to weak.

Foliage:

*Texture* (*both surfaces*).—Glossy, slightly leathery.
*Leaf arrangement.*—Alternate, clustered towards the top of the stems.
*Compound or single.*—Single.
*Quantity of leaves per lateral branch.*—12.
*Leaf shape.*—Elliptical to obovate.
*Leaf apex.*—Obtuse.
*Leaf base.*—Acuminate to acute.
*Leaf length.*—4.3 cm. in length.
*Leaf width.*—1.8 cm. in width.
*Pubescence.*—Slight (both surfaces).
*Pubescence color.*—175B to 175C.
*Leaf margin.*—Entire.
*Vein pattern.*—Arcuate.
*Young leaf color* (*upper surface*).—144A.
*Young leaf color* (*lower surface*).—147C.
*Mature leaf color* (*upper surface*).—139A.
*Mature leaf color* (*lower surface*).—147B.
*Vein color* (*lower surface*).—145B.
*Vein color* (*upper surface*).—145A.
*Leaf attachment.*—Petiolate.
*Petiole dimensions.*—8 mm. in length, slightly flattened 1.5 mm. in width, 1 mm. in height.
*Petiole color.*—145A.
*Durability of foliage to stress.*—Moderate.

Flower:

*Flower arrangement.*—Terminal clusters.
*Inflorescence type.*—Umbel.
*Inflorescence dimensions.*—Approx. 6 cm. in diameter and 4 cm. in height.
*Flowering habit.*—Continuously, once a year.
*Flower form.*—Double.
*Quantity of flowers per lateral stem.*—Approximately 3 to 8.
*Quantity of flower buds per lateral stem.*—Approximately 1 to 4.
*Quantity of flowers and buds per plant.*—Approximately 90, Approximately 3 flowers/bud.
*Flowering season.*—February to May.
*Time to flower or response time.*—Flowering 8 months after final pinching.
*Rate of flower opening.*—After the first flower of a cluster has opened, all flowers of that cluster will open in approximately 14 days.
*Fragrance.*—None.
*Self-cleaning or persistent.*—Persistent.
*Flower bud length.*—10 mm. in length.
*Flower bud diameter.*—6 mm. in diameter.
*Flower bud shape.*—Ovate.
*Bud color.*—145A.
*Rate of bud opening.*—95% in 14 days.
*Flower aspect.*—Upright to outward.
*Flower shape.*—Narrow funnel-campanulate.
*Flower dimensions.*—6 cm. in diameter and 3 cm. in height.
*Flower longevity.*—Lasts approximately 35 days on plant.
*Petal appearance.*—Dull, slightly velvety (both surfaces).
*Petal texture.*—Glabrous (both surfaces).
*Petal arrangement.*—Funnelfrom, rosette.
*Number of petals.*—Five in number.
*Petals fused or unfused.*—Lower 25 to 50% fused.
*Petal shape.*—Obovate.
*Petal margin.*—Entire.
*Petal apex.*—Obtuse.
*Petal dimensions.*—Approx. 3 cm. in length and 2 cm. in width.
*Petal color when opening* (*upper side*).—145C.
*Petal color when opening* (*under side*).—145C.
*Petal color when fully opened* (*upper side*).—56D.
*Petal color when fully opened* (*under side*).—56D.
*Petal color fading to.*—56D (base), 145C (apex).
*Petaloid appearance.*—Dull.
*Petaloid arrangement.*—Rotate in the center of the flower.
*Petaloid number.*—Approx. 7.
*Petaloid shape.*—Irregular, obovate to oblong.
*Petaloid margin.*—Entire, slightly undulate.
*Petaloid dimensions.*—0.8 cm. to 1.5 cm. in width and 2 cm. to 3 cm. in length.

*Petaloid color immature.*—145C.
*Petaloid color mature.*—56D.

Calyx:
*Calyx shape.*—Rosette.
*Calyx dimensions.*—1 cm. in diameter and 5 mm. in height.

Sepals:
*Sepal appearance.*—Pubescent on both surfaces.
*Sepal arrangement.*—Rosette.
*Number of sepals.*—Five in number.
*Sepals fused or unfused.*—Fused.
*Sepal shape.*—Rounded.
*Sepal margin.*—Entire.
*Sepal apex.*—Obtuse.
*Sepal base.*—Spatulate.
*Sepal dimensions.*—5 mm. in length and 3 mm. in width.
*Sepal color when opening* (*upper side*).—143C.
*Sepal color when opening* (*under side*).—143C.
*Sepal color mature* (*upper side*).—143C.
*Sepal color mature* (*under side*).—143C.

Bracts:
*Number of bracts.*—Between 10 and 15.
*Bract dimensions.*—13 mm. in length and 5 to 10 mm. in width.
*Bract shape.*—Rounded to oblong.
*Bract apex.*—Obtuse.
*Bract pubescence.*—Dense on under side, length 1.0 mm, color, 167C, upper side glabrous.
*Bract color* (*both sides*).—144C (base), 143A (apex).

Pedicels:
*Pedicel dimensions.*—3 to 5 mm. in length.
*Pedicel angle.*—75°.
*Pedicel color.*—145B.
*Pedicel pubescence.*—Strong, length 0.5 mm, color 192D.
*Pedicel strength.*—Moderate to strong.

Reproduction organs:
*Stamen number.*—Between 0 and 5, mostly mutated to petaloids.
*Anther shape.*—Dorsifixed, oval.
*Anther dimensions.*—1.5 mm.
*Anther color.*—167C.
*Filament length.*—15 mm.
*Filament color.*—67D.
*Amount of pollen.*—Very low.
*Pistil number.*—1 in number.
*Pistil dimensions.*—2.5cm. to 3.0 cm. in length.
*Stigma shape.*—Round.
*Stigma color.*—144C.
*Style length.*—2.0 to 2.5 cm.
*Style color.*—144C.
*Ovary color.*—143A.

Fruit and seed: Fruit and seed production has not been observed to date.

Disease and pest resistance: Plants of the new *Rhododendron* have not been observed for disease or pest resistance to date.

The invention claimed is:

1. A new and distinct variety of *Rhododendron* plant named 'HORT13' as described and illustrated.

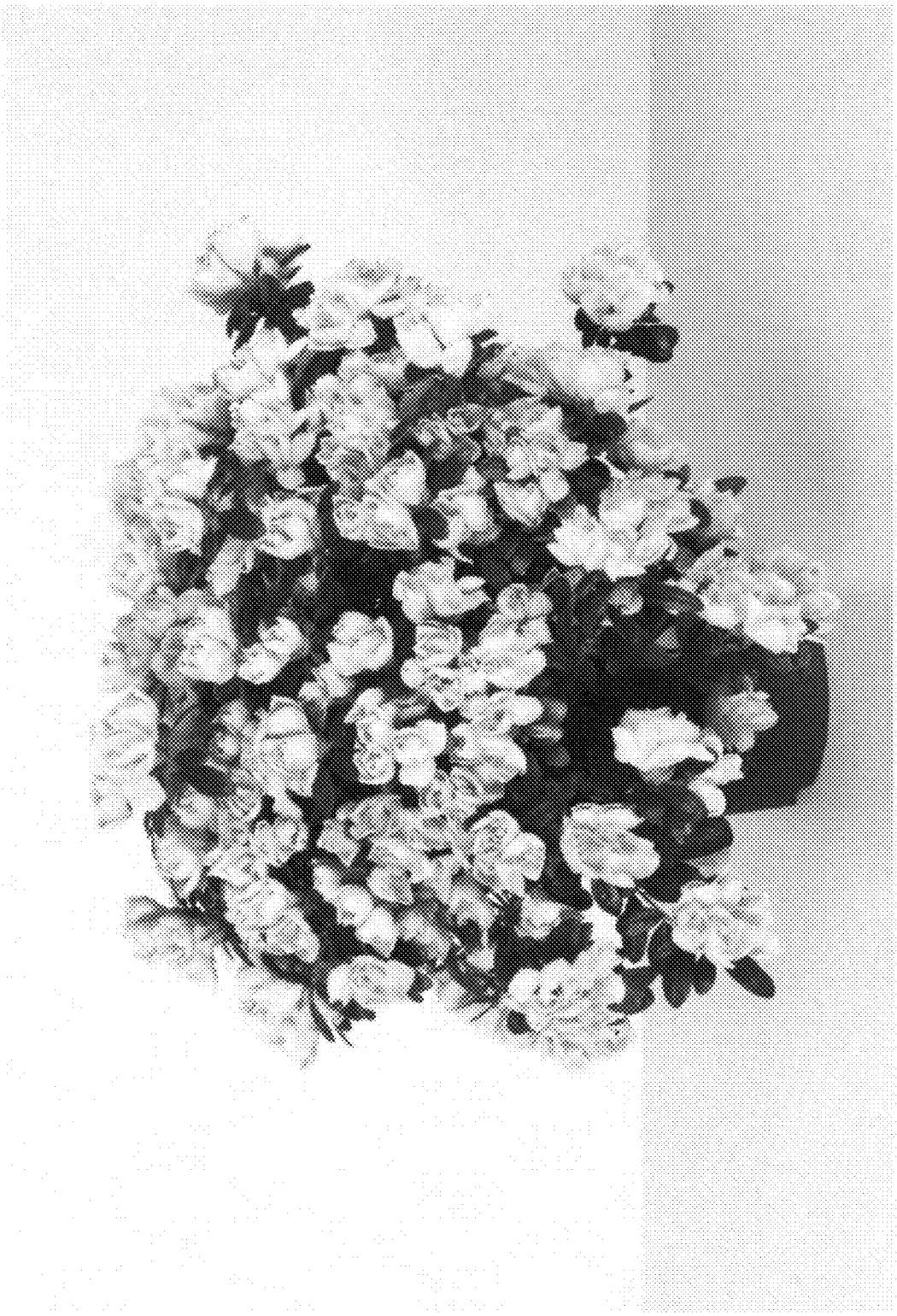

* * * * *